United States Patent [19]

Phillips

[11] Patent Number: 5,324,254
[45] Date of Patent: Jun. 28, 1994

[54] TOOL FOR LAPAROSCOPIC SURGERY

[76] Inventor: Edward H. Phillips, 712 N. Roxbury Dr., Beverly Hills, Calif. 90210

[21] Appl. No.: 4,056

[22] Filed: Jan. 13, 1993

Related U.S. Application Data

[62] Division of Ser. No. 528,954, May 25, 1990, Pat. No. 5,195,958.

[51] Int. Cl.$^5$ .................. A61B 17/39; A61B 17/36; A61B 17/22
[52] U.S. Cl. ................................. 604/21; 606/14; 606/41; 606/45
[58] Field of Search ............... 604/21, 27, 33–35, 604/39, 43, 249, 275, 902; 606/2, 10, 13, 15, 16, 27–31, 40, 41, 45, 46, 47, 49; 433/80, 82, 84, 85, 95, 100

[56] References Cited

U.S. PATENT DOCUMENTS

| | | | |
|---|---|---|---|
| 2,031,020 | 2/1936 | Wappler | 606/46 |
| 2,669,233 | 2/1954 | Friend | 604/33 |
| 2,812,765 | 11/1957 | Tofflemire | 604/32 |
| 2,888,928 | 6/1959 | Seiger | 606/49 |
| 3,085,573 | 4/1963 | Meyer et al. | 604/33 |
| 3,623,483 | 11/1971 | Dyer | 604/902 |
| 3,774,612 | 11/1973 | Marco . | |
| 3,850,175 | 11/1974 | Iglesias | 606/46 |
| 3,874,083 | 4/1975 | Buckley | 433/80 |
| 3,939,839 | 2/1976 | Curtiss | 606/46 |
| 3,974,833 | 8/1976 | Durden . | |
| 4,083,706 | 4/1978 | Wiley . | |
| 4,149,315 | 4/1979 | Page, Jr. et al. | 604/249 |
| 4,193,406 | 3/1980 | Jinotti | 604/33 |
| 4,227,878 | 10/1980 | Löhn | 433/80 |
| 4,451,257 | 5/1984 | Atchley | 604/33 |
| 4,487,600 | 12/1984 | Brownlie et al. . | |
| 4,492,230 | 1/1985 | Sunago et al. | 606/13 |
| 4,593,691 | 6/1986 | Lindstrom et al. | 606/49 |
| 4,680,026 | 7/1987 | Weightman et al. | 604/33 |
| 4,886,491 | 12/1989 | Parisi et al. | 604/902 |
| 5,098,416 | 3/1992 | Imonti | 604/902 |
| 5,151,097 | 9/1992 | Daikuzono | 606/16 |
| 5,186,714 | 2/1993 | Boudreault et al. | 606/49 |
| 5,190,541 | 3/1993 | Abele et al. | 606/49 |
| 5,195,958 | 3/1993 | Phillips | 604/33 |

FOREIGN PATENT DOCUMENTS

| | | |
|---|---|---|
| 0327410 | 9/1989 | European Pat. Off. . |
| 0463363 | 1/1992 | European Pat. Off. . |
| 3209444 | 10/1982 | Fed. Rep. of Germany . |
| 2287918 | 5/1976 | France . |
| 2443829 | 7/1980 | France . |
| 2513109 | 3/1983 | France . |
| 9003152 | 4/1990 | PCT Int'l Appl. . |
| 2117245 | 10/1983 | United Kingdom . |
| 2147209 | 5/1985 | United Kingdom ......... 606/16 |

Primary Examiner—Ralph Lewis
Attorney, Agent, or Firm—Frederick Gotha

[57] ABSTRACT

The invention relates to a instrument for laparoscopic surgery which permits the operating surgeon to irrigate or suction the operative area while performing electrocautery or laser hemostasis and dissection of body tissue with the same instrument.

The invention also relates to a laparoscopic tool for evacuating free stones or blood clots from the operating area which are to large to be suctioned from the body cavity or to remove gallstones from a gallbladder which has been distended by stones and cannot be retrieved through an umbillical sheath.

3 Claims, 9 Drawing Sheets

TOOL FOR LAPAROSCOPIC SURGERY

This application is a division of U.S. application Ser. No. 07/528,954 filed May 25, 1990 and now U.S. Pat. No. 5,195,598.

FIELD OF THE INVENTION

This invention relates to a tool for use in laparscopic surgery.

BACKGROUND OF THE INVENTION

Utilizing a high definition video monitor, a surgical team can perform operating techniques internal to the human body which are minimally invasive through the use of a laparoscope equipped with a television camera. The laparoscopic technique has been used to remove diseased gallbladders and stones by using a laser for hemostasis and disection of the gallbladder from the liver bed. Before the gallbladder is removed, the liver bed area is lavaged and irrigated, and suctioned. In order to irrigate or suction the liver bed area, the operating surgeon is required to temporarily abandon another instrument which he is manipulating when irrigation or fluid evacuation is desired. To avoid an increase in operating time which compromises the safety of the patient, an operating assistant is utilized to control the instrument which would otherwise be temporarily abandoned by the operating surgeon. Although the above discussion of the prior art was concerned with laparoscopic laser removal of the gallbladder, the identical procedure is used where the hemostatis and disection of the gallbladder from the liver bed is to be achieved by the use of electrocautery.

Conventionally, after the gallbladder is freed from the liver, a grasping forcep is used to pull the gallbladder through an umbillical sheath. In the event of free gallstones or clots which are too large to be suctioned from the operative area, a grasping tool must be used to grasp such stones or clots which are then singularly removed from the body cavity or operating area. This procedure increases the time of the operation which increases the risk of the surgery. If there are stones in the gallbladder which are too large to come into the umbillical sheath, the gallbladder must be teased through the fascial opening after the sheath is pulled through the fascia. Should it not be possible for the gallbladder to be teased through the fascial opening, an incision must then be made which will then permit the gallbladder to be removed from the body. When there are numerous gallstones in the gallbladder, the stones will distend the lower portion of the gallbladder as the gallbladder is being teased through the fascial opening thereby forming an enlarged diametric cross-section which prevents removal of the gallbladder through the fascial opening. This again requires an incision to remove the gallbladder and further increases the risk of surgery.

Present techniques for laparoscopic removal of the gallbladder from the liver bed constitute either a laser technique or an electrocautery technique. The electrocautery technique utilizes a coagulation hook for teasing away body tissue in the liver bed area to expose the gallbladder and the cystic artery and cystic duct after which the gallbladder is disected from the liver bed. The hook provides an advantage in teasing away tissue which is not available when a laser is used since the hook can physically lift the tissue before cutting. A laser on the other hand has the advantage of uniform cutting and prescise coagulation but without the capability of lifting the tissue, the depth of the cut must be estimated by the surgeon; too deep a cut will result in internal bleeding which must be stopped by coagulation.

SUMMARY OF THE INVENTION

There is, therefore, provided according to the present invention, a tool for laparoscopic surgery which permits the surgeon to irrigate or suction an internal body cavity laparoscopically without having to cease manipulation of other laparoscopic instruments and to provide for the rapid evacuation of stones and blood clots from an internal cavity such as the liver bed region or from a gallbladder which is being exteriorized or being pulled through the umbillical fascia. A tool is also provided which utilizes a combination of electrocautery and laser for laparoscopic surgery.

The present invention is directed to a surgical instrument for laparoscopic evacuation and collection of particulate matter such as blood clots or stones from a body cavity. The surgical tool is composed of a housing having an outlet port for the passage of evacuated fluid which has been suctioned from a body cavity and having an inlet port for the passage of irrigating fluid. The housing contains a first internal conduit which communicates with the outlet port and a second internal conduit which communicates with the inlet port. A third conduit having a proximate and distal end is carried by the housing. The third conduit communicates with the first and second conduits and has a distal end opening through which irrigating fluid may enter into the body cavity or through which fluid or particulate matter such as stones or blood clots may be evacuated by suctioning from the body cavity into the third conduit. In the preferred embodiment, a pair of push valves which are biased in a closed position are carried by the housing where the valves communicate with the third conduit for selectively permitting fluid flow between the third conduit and the first conduit or between the third conduit and the second conduit. Thus, irrigating fluid may be selectively admitted into the third conduit by opening one of the valves or fluid or particulate matter may be evacuated by opening the other valve. The valves are located adjacent to each other on the housing thereby permitting the surgeon to readily select either mode of operation without removing his hand from the instrument.

In another embodiment of the invention, the third conduit has an axially extending inner conduit which communicates with the first and second conduits of the housing. The distal end of the inner conduit has an orifice to permit the passage of evacuated fluid or irrigating fluid therethrough. An outer axially extending conduit has an opening at its distal end to permit the passage of irrigating fluid or evacuated fluid and particulate matter where the outer conduit surrounds the distal end of the inner conduit so as to form a collection region intermediate the distal end of the outer conduit and the distal end of the inner conduit. The outer conduit is slideably and telescopically mounted to the inner conduit so as to permit relative axial movement therewith such that the volume of the collection region may be varied. The distal end of the outer conduit at the opening therein contains a lip extending radially from the axis of the outer conduit so as to form a scoop for scooping free stones or blood clots into the collection chamber which are too large to be suctioned through the inner conduit.

In another embodiment of the invention, a nozzle member having a longitudinal axis is carried by the housing and has an irrigation and vacuum conduit extending therethrough which communicates with the first and second conduits contained in the housing to permit the passage of irrigating and evacuating fluids into and from the body cavity. The nozzle member has a axially extending channel which extends therethrough and is in fixed spaced relationship and substantially parallel to the vacuum and irrigation conduit and has an electrocautery hook outlet port communicating with the channel at the distal end of the nozzle. The housing contains a pair of push valves which are biased in a normally closed position and communicate with the irrigation and vacuum conduit of the nozzle when opened. The surgeon may selectively irrigate or evacuate while simultaneously utilizing the electrocautery hook to lift, tease, and disect body tissue. Thus, the operating surgeon can manipulate the irrigation, evacuation or electorcautery simultaneously without having to temporarily abandon another laparoscopic instrument being used in the operation.

In another embodiment of the invention, the nozzle has an electrocautery hook fixed at its distal end and contains a channel axially extending therethrough. The axially extending channel communicates with an outlet port to permit the passage of evacuated fluid and also communicates with an inlet port to permit the passage of irrigating fluid. A laser fiberoptic bundle is insertable into the channel through a side port located near the proximate end of the nozzle and can be extended through the distal opening of the nozzle thereby allowing the surgeon to utilize both electrocautery and laser techniques without having to introduce an additional laparoscopic tool.

BRIEF DESCRIPTION OF THE DRAWINGS

These and other features and advantages will become appreciated as the same become better understood with reference to the following specification, claims and drawings wherein:

DETAILED DESCRIPTION

Figure 1:
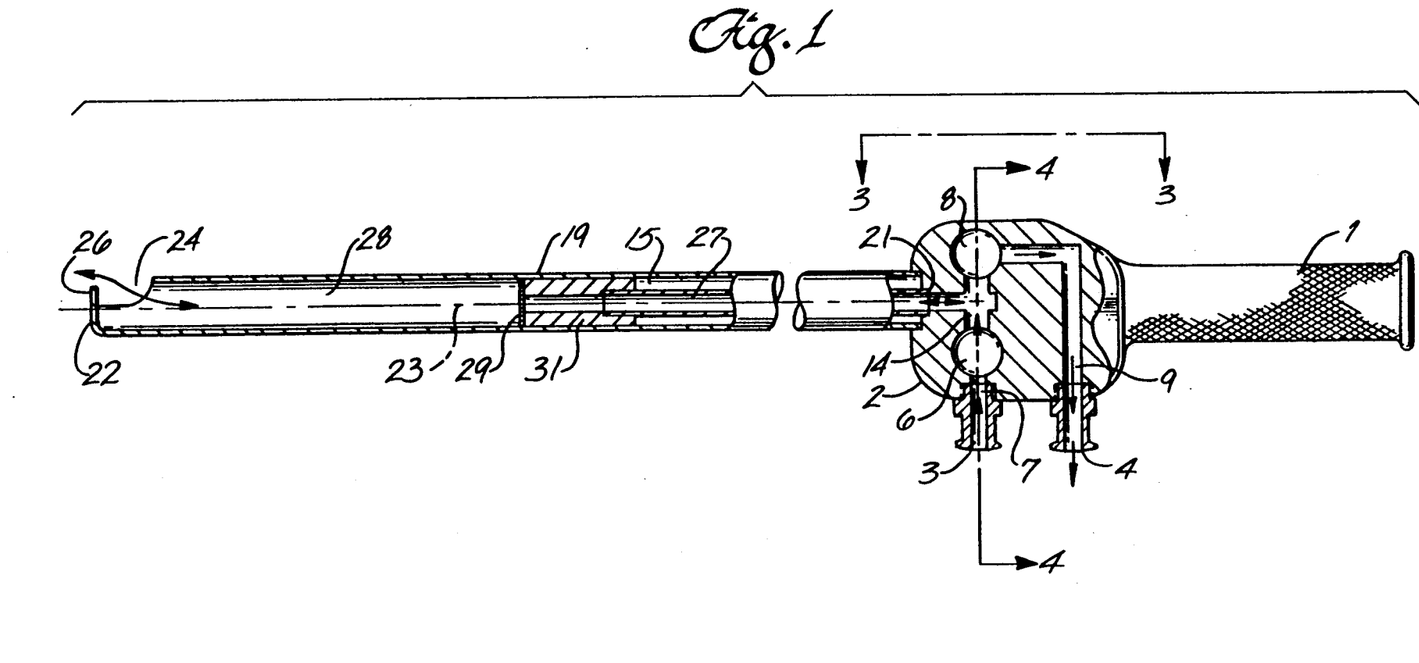
FIG. 1 is a cross-section view of an embodiment of a laparoscopic tool illustrating the present invention.
Figure 4:
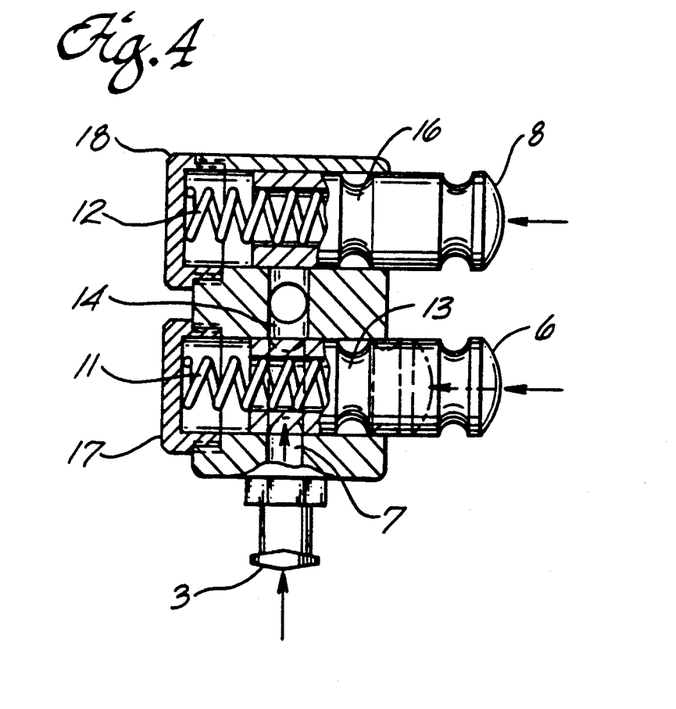
FIG. 4 is a cross-section in the direction of line 4—4 shown on FIG. 1.

FIG. 1 shows a laparoscopic tool for irrigation and collection of evacuated fluid and particulate matter in cross-section with the distal end being shown on the left. Adjacent the hand piece 1 is a housing 2 where the housing is shown in partial cross-section having an irrigating inlet port 3 and a vacuum outlet port 4. The mechanisms for supplying irrigating fluid to the irrigating inlet port and for providing suction at the vacuum outlet port are well known in the prior art and not herein described. A pair of push valves are shown in top view in FIG. 1 where push valve 6 communicates with irrigating inlet port 3 by an inner conduit 7. Likewise, vacuum outlet port 4 communicates with push valve 8 through a second inner conduit 9. As shown in FIG. 4, push valves 6 and 8 are biased in a closed position by spring members 11 and 12. When the push valve is sufficiently depressed as shown in FIG. 4, annular grove 13 is aligned with inner conduit 7 thereby permitting irrigating fluid to flow past irrigating inlet port 3 and into the common duct 14. Similarly, when push valve 8 is sufficiently depressed, annular grove 16 is aligned with the second inner conduit 9 thereby permitting evacuated fluid to pass through second inner conduit 9 and flow through vacuum outlet port 4. Referring again to FIG. 4, it can be seen that biasing springs 11 and 12 bear respectively against the inner head portions of knurled fasteners 17 and 18.

Referring again to FIG. 1, a third conduit or shaft member 19 has a proximate end 21 which is secured to the housing 2 and a distal end 22. The third conduit or shaft member 19 has a longitudinal axis 23 and adjacent or near the distal end 22 an opening 24 which is bounded at the distal end by lip 26; lip 26 forms the terminating end of the third conduit or shaft member 19 and in conjunction with opening 24, forms a scoop for the removal of stones or particulate matter such as blood clots from an internal body cavity. Terminating at the proximate end of the third conduit or shaft member 19 is an internal passageway 27 which communicates with a collection chamber 28. Both collection chamber 28 and internal passageway 27 have axis which are coaxial with the third conduit or shaft member 19. A screen 29 is inserted intermediate collection chamber 28 and internal passageway 27 so as to preclude the entry into the internal passageway of stones or clots which would act as a barrier to the flow of evacuated fluid through the third conduit or shaft member 19. A plug 31 abuts against screen 29 and has an opening therethrough which communicates with both passageway 27 and collection chamber 28 thereby providing a continuous path from the orifice 24 to the proximate end of the third conduit or shaft member 19. As can be seen in FIG. 1, the internal passageway 27 communicates with the common duct 14 of the housing at the proximate end of the third conduit or shaft member 19. Thus, by pressing push valve 6, the surgeon opens the valve and permits irrigating fluid to flow through the third conduit or shaft member and out of the shaft member at opening 24. If the surgeon desires to suction the body cavity to evacuate fluid and particulate matter, push valve 8 is depressed thereby opening the valve and permitting communication between the second inner conduit 9 and internal passageway 27.

Figure 2:
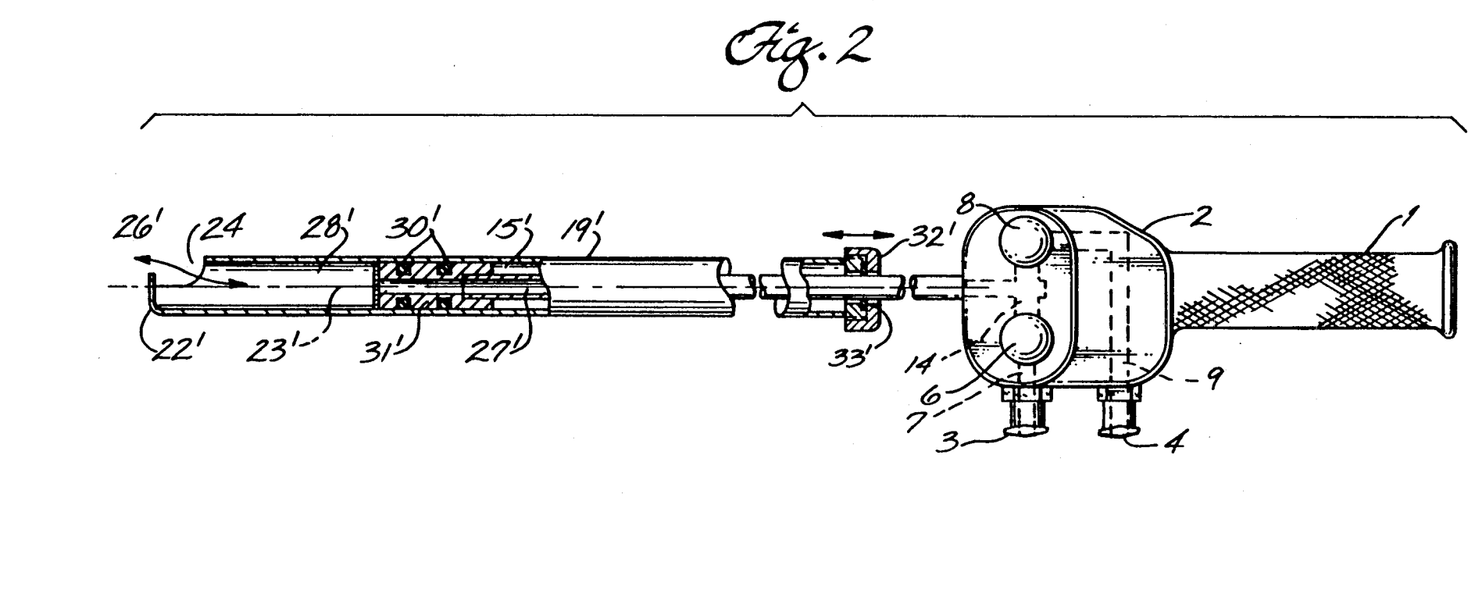
FIG. 2 is a cross-section view of a laparoscopic instrument illustrating another embodiment of the invention.
Figure 3:
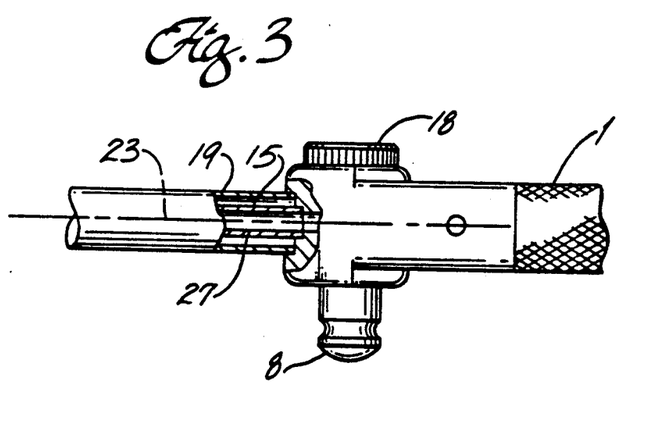
FIG. 3 is a partial cross-section of FIG. 1 in the direction of line 3—3 shown on FIG. 1.

Another embodiment of the invention is shown in FIG. 2. In this embodiment, the collection chamber 28' may be varied in volume. The shaft member 19' is telescopically and slideably mounted to tubular member 27' for relative axial movement therewith. It can be seen in FIG. 2 that tubular member 27' at its distal end is capatively held by plug member 31' where the plug member 31' has a pair of O-rings 30' to prevent the passage of evacuated fluid into the region 15' surrounding tubular member 27' and interior to the inside wall of shaft member 19'. To effectuate relative movement between shaft 19' and tubular member 27', it can be seen that at the proximate end of shaft 19' a nut member 32' has a seal 33' which surrounds the tubular member such that by hand pressure applied to adjustment nut 32', the shaft member 19' will move relative to the tubular shaft thereby increasing or decreasing the volume of collection chamber 28'. The structure of the housing shown in FIG. 2 is identical to that which is shown in FIG. 1 and is accordingly so represented in FIG. 2. In either of the embodiments, the surgeon may irrigate the body cavity by depressing push valve 6 or suction the body cavity by depressing push valve 8. The essential difference between the embodiments of the invention shown in FIGS. 1 and 2 is that in the embodiment shown in FIG. 2, the volume of the collection chamber can be selectively varied by the surgeon.

Although not shown, a three-way valve could perform the function performed by the pair of push valves described above. The three-way valve could be selectively positioned in a first position so as to permit the flow of irrigating fluid or selectively placed in a second position which would preclude the flow of irrigating fluid and allow the flow of evacuated fluid through the instrument. A neutral position would be provided so as to preclude the flow of either irrigating or evacuated fluid.

Figure 5:
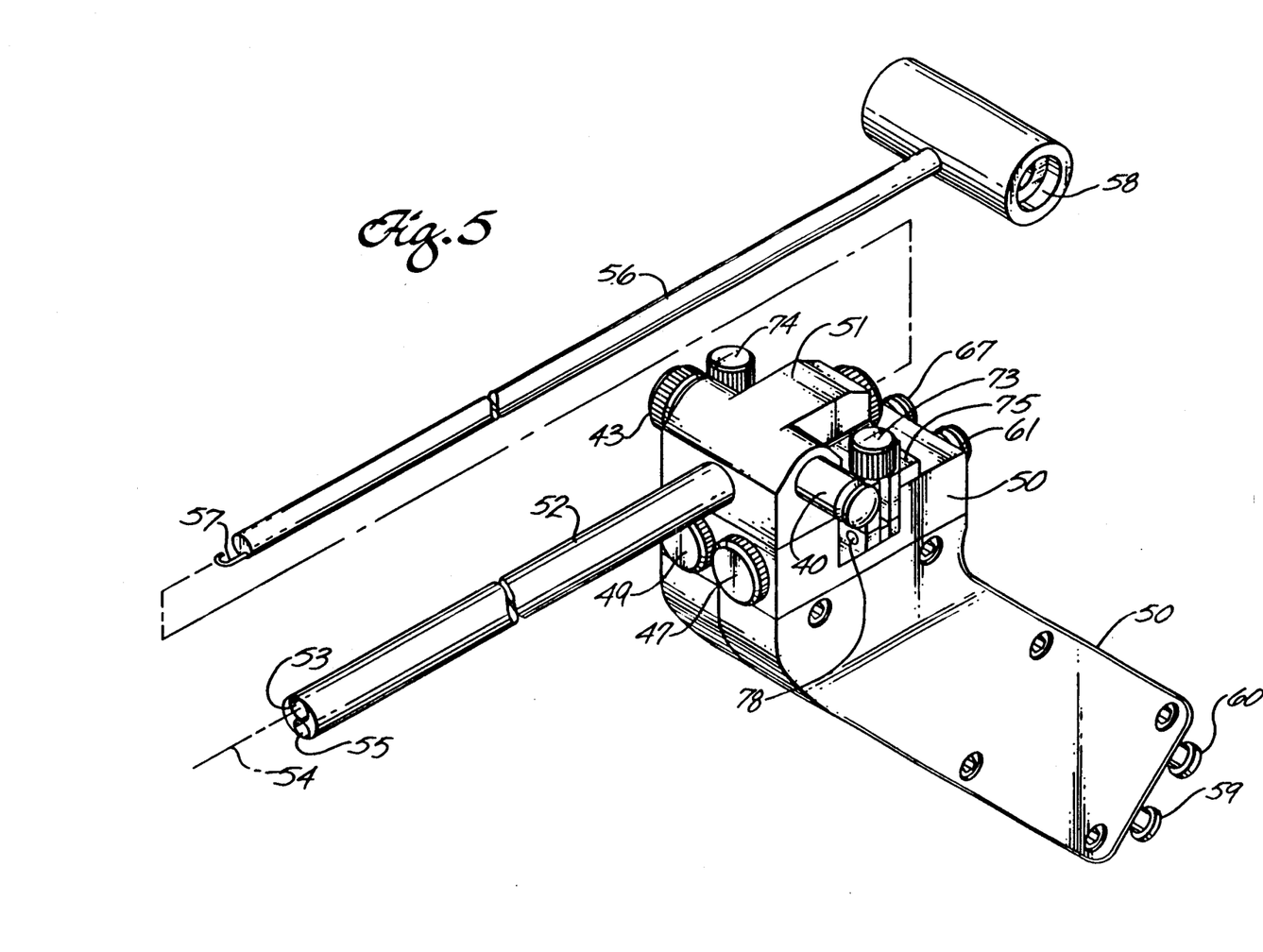
FIG. 5 is a perspective view of another embodiment of the invention illustrating the handpiece and the electrocautery hook.
Figure 9:
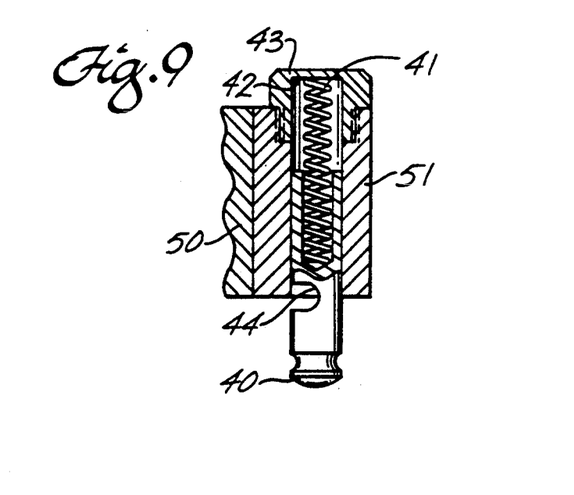
FIG. 9 is a cross-section in the direction of line 9—9 shown on FIG. 7.

Another embodiment of the invention is shown in FIG. 5 which illustrates a hand piece 50 shown in perspective that has a removeably mounted attachment 51 and a shaft 52 extending therefrom. Shaft 52 contains an internal channel 53 and a longitudinal axis 54 where internal channel 53 extends axially through shaft member 52. Located below internal channel 53 and substantially parallel thereto is an axially extending irrigation and evacuation conduit 55. Also shown in perspective FIG. 5 is an electrocautery member 56 which has a hook 57 extending from its distal end. As can be seen in FIG. 5, electrocautery member 56 is insertable into internal channel 53. This is accomplished by depressing tunnel bolt 40 which is biased by a spring 41 that bears against the inside head wall 42 of the knob 43. Referring to FIG. 9, the tunnel bolt 40 is shown before insertion of electrocautery member 56; the tunnel bolt has a transverse slot 44 which is moved into alignment with channel 53 by depressing the tunnel bolt thereby permitting the electrocautery member 56 to be inserted through the transverse slot 44 and into internal channel 53. After insertion into the channel, the hook extends beyond the distal end of the shaft member 52. The body of electrocautery member 56 is insulated and has electrical terminals at its proximate end to which an electrical voltage can be applied selectively by the surgeon so as to rapidly increase the temperature of hook 57 thereby permitting cauterizing and dissecting of body tissue. The electrical contacts, circuitry and voltage supply are not shown in the drawings since they are commonly known to one skilled in laparoscopic surgery utilizing an electrocautery instrument.

Figure 6:
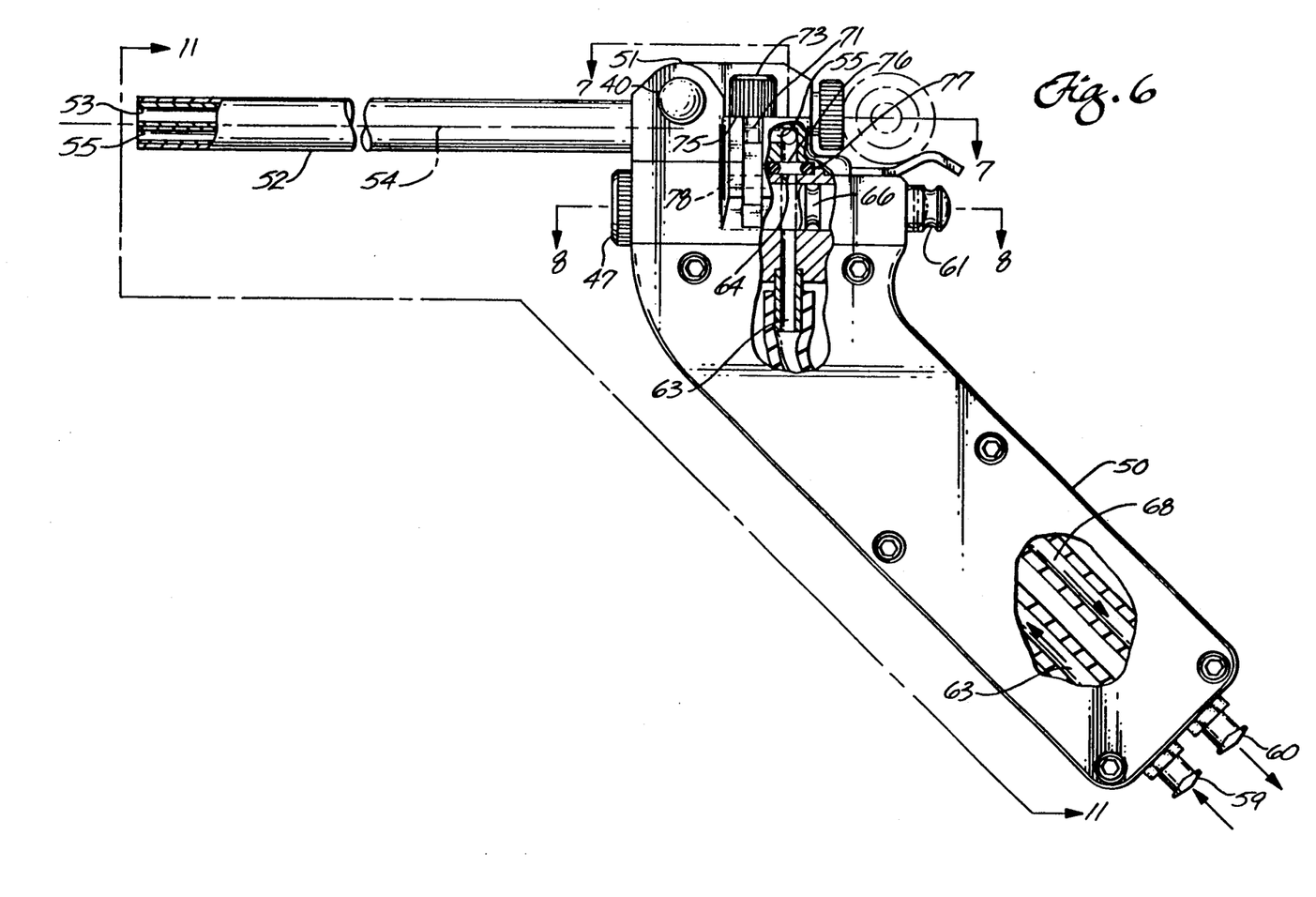
FIG. 6 is an elevational view of the embodiment shown in FIG. 5 in partial cross-section.
Figure 7:
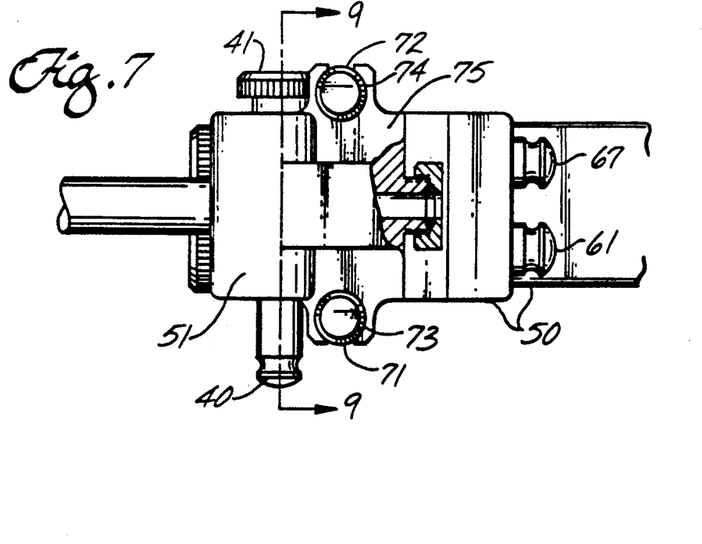
FIG. 7 is a cross-section in the direction of line 7—7 shown on FIG. 6.
Figure 8:
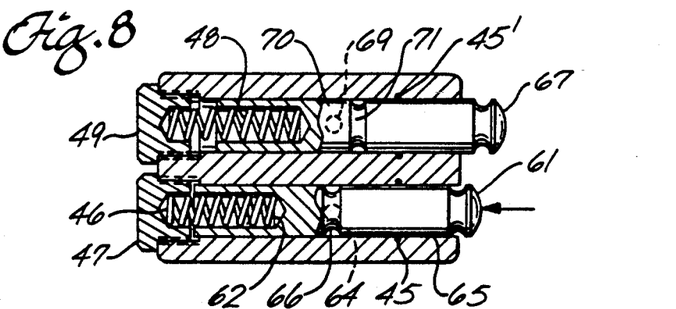
FIG. 8 is a cross-section in the direction of line 8—8 on FIG. 6.

Referring now to FIG. 6, the handpiece 50 has an irrigating fluid inlet 59 and an evacuated fluid outlet Communicating with irrigating fluid outlet 59 is a push valve 61 which is biased in a normally closed position by spring member 62 where spring member 62 bears against the inside head wall 46 of thumb nut 47. Inner conduit 63 communicates with irrigating fluid inlet 59 and has an outlet port 64 which is normally covered by the outer periphery 65 of push valve 61. As can be seen in FIG. 8, push valve 61 has an annular groove 66 which may be moved into alignment with outlet port 64 by the operator of the instrument by depressing push valve 61. This allows irrigating fluid to flow past the valve and into attachment 51. In a like manner, evacuated fluid may be evacuated from the body cavity and pass through attachment 51 by depressing push valve 67 biased by spring 48 that bears against thumb nut 49. As can be seen in FIG. 8, a seal 45 engages the outer periphery 65 of push valve 61 and similarly seal 45' engages the periphery 70 of push valve 67. Push valve 67 communicates with inner conduit 68 which in turn communicates with evacuated fluid outlet 60. The mechanisms for pumping irrigating fluid and for suctioning evacuated fluid through ports 59 and 60 are known in the prior art and are not described herein. Referring again to FIG. 8, it can be seen that a inlet port 69 for evacuated fluid is in a normally closed position because of being covered by the outer periphery 70 of push valve 67. Annular grove 71 may be moved axially by the surgeon into alignment with inlet port 69 by depressing push valve 67 thereby permitting evacuated fluid to flow into handpiece 50 and subsequently pass through evacuated fluid outlet port 60. As can be seen in FIGS. 5 and 6, attachment 51 is removeably mounted to handpiece 50 by hinged screws 71 and 72 which are hinged to handpiece 50 by pivot pins 78 and 79 and have captive nuts 73 and 74 which can be tightened so as to bear against bearing surface 75. The hinge screws are pivotally mounted to handpiece 50 such that when attachment 51 is mated to handpiece 50, the hinged captive screws may be rotated upward into a vertical position and the nuts thereafter tightened so as to bear against surface 75 to effectuate a lock between attachment 51 and handpiece 50. Attachment 51 has an irrigating inlet port 76 which, after attachment 51 is mated to handpiece 50, communicates with outlet port 64 which in turn communicates with inner conduit 63. Located intermediate outlet port 64 and inlet port 76 an O-ring seal 77 is utilized to effectuate a seal. Thus, the surgeon, by depressing push valve 61 will open outlet port 64 to permit irrigating fluid to flow into conduit 55 and discharge into the body cavity at the distal end of shaft 52. Likewise, by depressing push valve 67, evacuated fluid may be suctioned into conduit 55 from the body cavity and thereafter flow to evacuated fluid inlet port 69 and then through inner conduit 68 for discharge through outlet 60.

Figure 10:
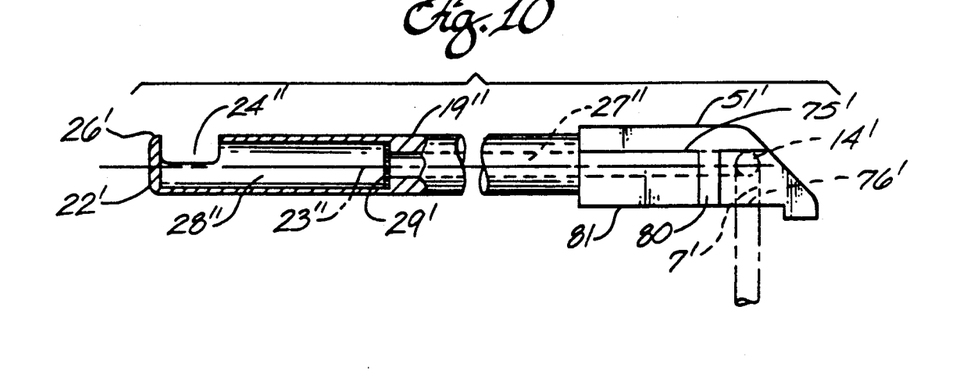
FIG. 10 is a partial cross-sectional side view of another embodiment of the invention, illustrating a removeably attachable member for the collection of stones or other particulate matter from the body cavity.
Figure 11:
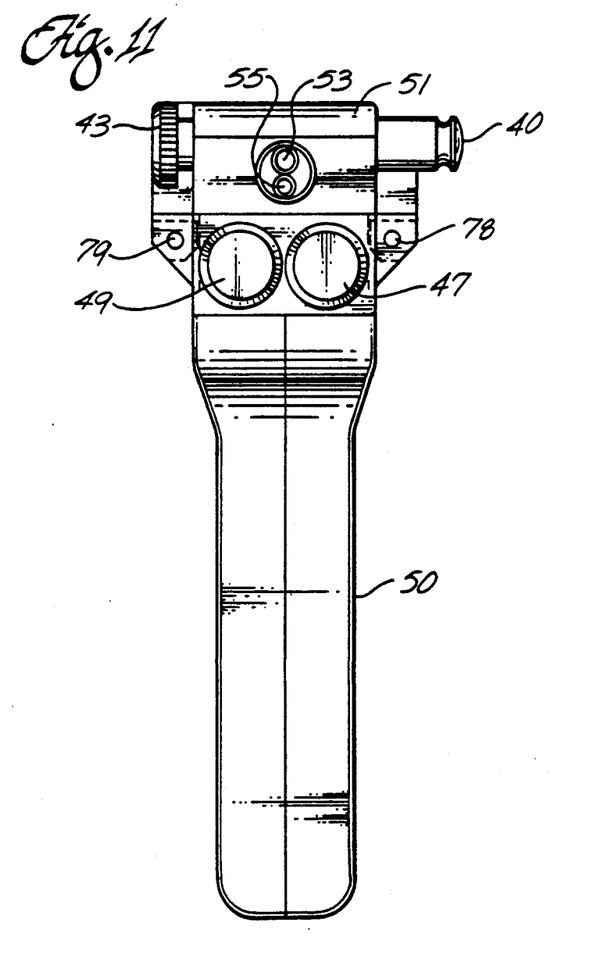
FIG. 11 is a front view in the direction of line 11—11 shown on FIG. 6.

Another embodiment of the invention is illustrated in FIG. 10 where the attachment member 51' is shown detached from the handpiece 50. The construction of attachable member 51' embodys a shaft or conduit member 19" which has a distal end to the left 22" and a longitudinal axis 23". An axially extending internal passageway 27" communicates with a collection chamber 28" which is formed at the distal end of shaft or conduit member 19". An opening 24" is shown at the distal end of conduit member 19" which is bounded by a lip 26" and the axially extending wall of the shaft or conduit member 19". At the juncture of internal passageway 27" and the collection chamber 28", screen 29" is interposed to preclude the passage of stones or particulate matter into channel 27". A scoop is thus formed for the evacuation of particulate matter from the operative area. At the right or proximate end of detachable member 51 is a slot 80 into which the hinged screw 71 may be rotated when attachable member 51 is to be mated to the handpiece 50. To accomplish a lock, the captive nuts are screwed down on to the captive screws 72 against the bearing surface 75' to effectuate a lock in the same manner as detachable member 51 was locked to handpiece 50 in the previously described embodiment of the invention. As can be seen in FIG. 10, passageway 27" communicates with irrigating outlet port 76' and with an evacuating fluid outlet port which is not shown on FIG. 10 but is positioned laterally from inlet port 76' on the mating surface 81 of the attachable member 51'. A common duct 14' communicates with internal passageway 27" and inner conduit 7' for irrigating fluid and internal passageway 27" also communicates through common duct 14' with an inner conduit not shown in the drawing in FIG. 10 for evacuating fluid through the inlet port 69 shown on FIG. 8. Thus, a tool for irrigation and collection of stones and other particulate matter such as blood clots is provided which can be removeably mounted to the handpiece 50.

Figure 12:
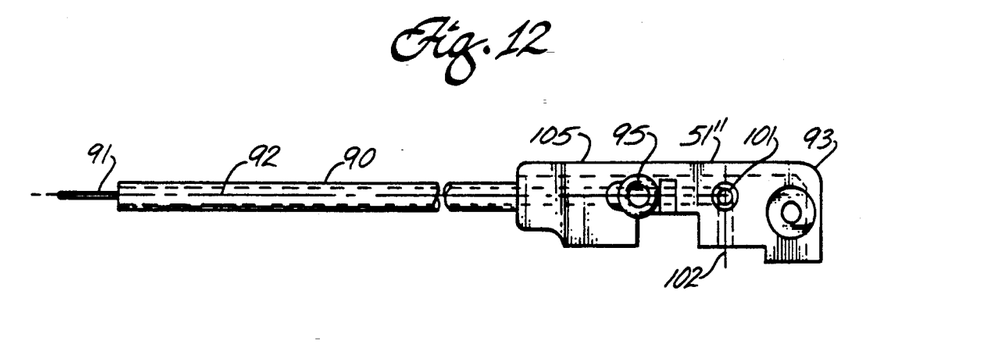
FIG. 12 is a side view of another embodiment of the invention illustrating the handpiece attachment for the laser and electrocautery combined surgical functions.
Figure 13:
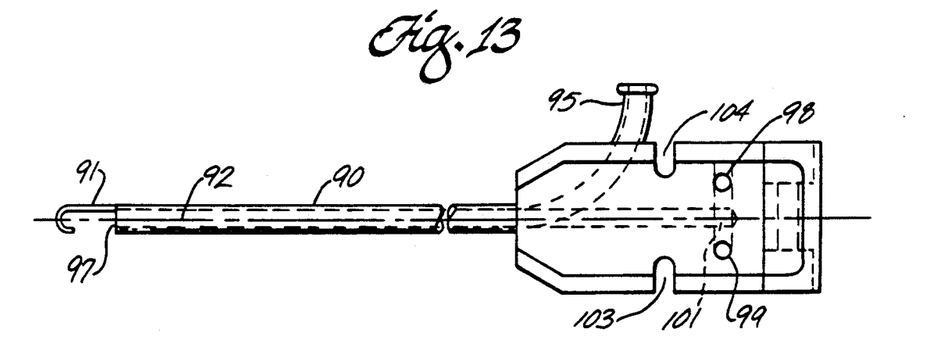
FIG. 13 is a top view of FIG. 12.

In yet another embodiment of the invention illustrated in FIGS. 12 and 13, a combined laser and electrocautery attachment 51" to the handpiece 50 is shown separated from the handpiece. Referring to FIG. 12, attachable member 51" has an insulated tube 90 which has extending from its distal end electrocautery hook member 91. Insulated tube 90 has an internal passageway 92 extending longitudinally through the tube for the passage of irrigating or evacuated fluid. At the proximate end of attachment member 51" a housing 93 is illustrated which contains a banana plug receptacle 94 for delivering electrical current to the electrocauterizing hook 91. A side port 95 extends through the housing and communicates with internal passageway 92 where a laser fiberoptic bundle 96 may be inserted through the side port 95 and into internal passageway 92, thereafter be extended through the orifice 97 located at the terminus of insulated tube 90 at its distal end.

Referring to FIG. 13 which is a bottom view of FIG. 12 it can there be seen that the housing 93 contains an irrigating fluid inlet port 98 and an evacuated fluid outlet port 99 which align respectively with irrigating outlet port 64 of the handpiece 50 and with inlet fluid evacuation port 69 of the handpiece. A common duct 101 shown on FIG. 12 communicates with irrigating inner conduit 102. Located directly behind inner conduit 102 is an evacuating fluid inner conduit which communicates with common duct 104 and evacuated fluid outlet port 99. Housing 93 is insulated to prevent the grounding of housing 93 to handpiece 50 when attachment member 51" is attached to the handpiece. The hinged screws 71 and 72 pivot into slots 103 and 104 and the captive nuts 73 and 74 of handpiece 50 can be tightened to bear against the surface 105 of housing 93. Irrigating fluid inlet port 98 aligns with irrigating outlet 64 of handpiece 50 and evacuated fluid outlet 99 aligns with inlet port 69 of handpiece 50 such that the push valves may be selectively opened by the surgeon thereby permitting irrigating fluid to flow through passageway 92 and into the body cavity through orifice 97 or fluid may be evacuated from the body cavity through past orifice 97 and through internal passageway 92 and evacuated from the handpiece 50 through evacuated fluid outlet port 60.

Figure 14:
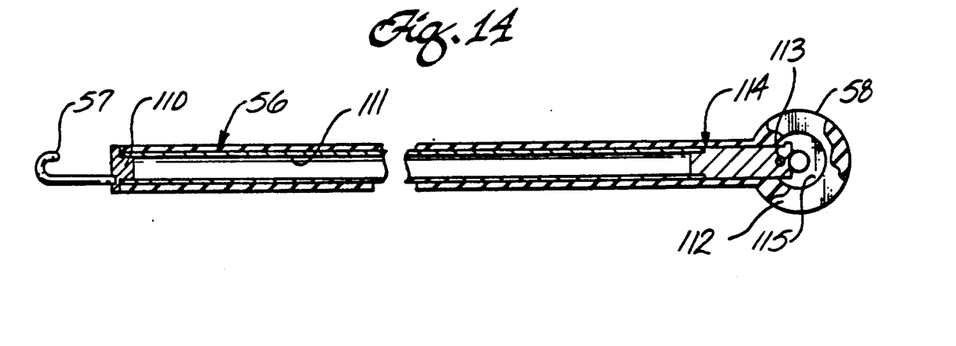
FIG. 14 is a side sectional view of an electrocautery device.
Figure 15:
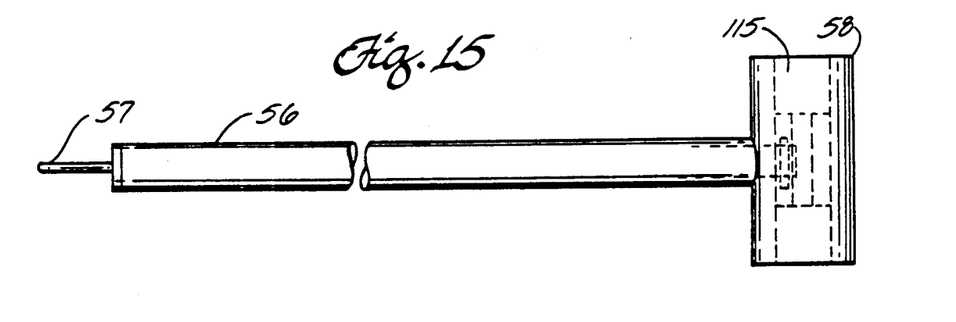
FIG. 15 is a top view of FIG. 14.

FIG. 14 is a sectional side view of the electrocautery member 56 shown on FIG. 5. Hook 57 is a metallic member which can conduct an electrical current and is brazed to stainless steel plug 110 which is brazed to a metal conductive tube 111. The exterior portion of the metal tube 111 is covered by electrical insulative material 102 which surrounds the tube for its entire length. At the proximate end 58 of the electrocautery member 56, an insulating bushing 112 is attached by pin 113 to metal tube 111 where pin 113 extends into a copper bushing 114 which is brazed to metal conductive tube 111. A banana plug (not shown) inserts into the banana plug receptacle 115 where the electrical lead of the banana plug contacts copper bushing 114. An external power source is utilized to deliver direct current to the banana plug which when plugged into banana plug receptacle 115 completes the electrical circuit.

Figure 16:
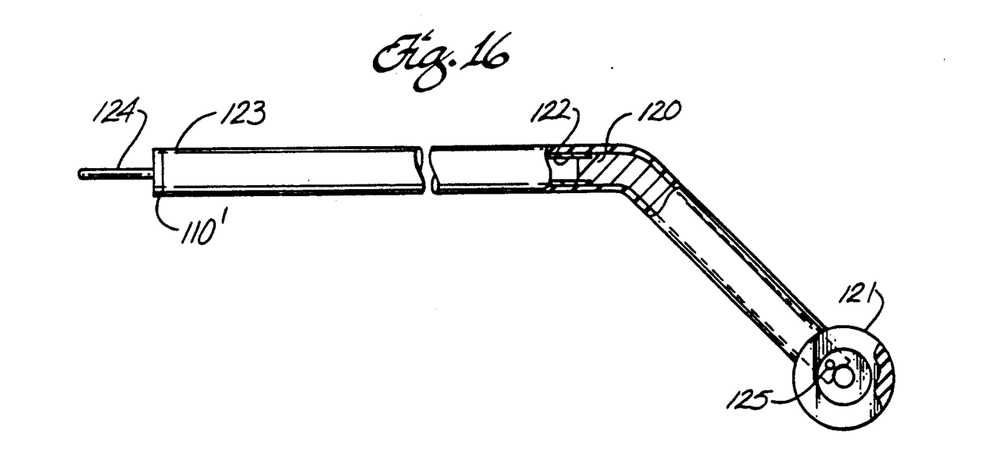
FIG. 16 is a side sectional view of another embodiment of an electrocautery device.

Another embodiment of an electrocautery member is shown in FIG. 16. As can be seen, a copper bushing 120 extends into insulating bushing 121 where said insulating bushing is made of an electrical insulating material. The copper bushing 120 is brazed to a metal conductive tube 122 which extends longitudinally and has an end 123 where stainless steel plug 110' is brazed into the end of the tube. A metallic hook 124 extends from the tube and is in electrical contact with it. Surrounding the metal conductive tube is a layer of electrical insulation in the same manner as shown in FIG. 14. As in the embodiment shown in FIG. 14, the insulating bushing 121 is pinned 125 to copper bushing 120. The banana plug receptacle and the function of the receptacle is identical to that described above.

While I have shown and described certain embodiments of the present laparoscopic surgical tool, it is to be understood that it is subject to many modifications without departing from the spirit and scope of the claims as recited herein.

What is claimed is:

1. A combined laser and electrocautery tool, comprising:
    (a) a housing having a proximate end and a distal end, a longitudinal axis, and a side port for the passage of a laser fiber optic bundle;
    (b) an insulated metal tube carried by said housing and having a distal and proximate end and a longitudinal axis and an internal passageway extending axially therethrough, where said insulated metal tube extends axially in a distal direction from said distal end of said housing and said housing has a common duct communicating with said side port and said internal passageway to permit the passage of said fiber optic bundle into said internal passageway;
    (c) an electrocautery member extending axially from said distal end of said insulated tube and in electrical communication with said metal tube;

(d) said housing further comprising an inlet port communicating with said common duct for the passage of irrigating fluid and an outlet port communicating with said common duct for the passage of evacuated fluid from a body cavity, said housing having a receptacle therein adapted for receipt of an external electric power source for electrical communication with said metal tube.

2. The combined laser and electrocautery tool recited in claim 1 wherein said electrocuatery member is a hook.

3. The combined laser and electrocautery tool recited in claim 1 wherein said housing is insulated.

* * * * *